United States Patent [19]
Brandon et al.

[11] Patent Number: 5,210,077
[45] Date of Patent: May 11, 1993

[54] ANTIBODIES TO CYTOKININS HAVING A GLYCOSYLATED ISOPRENOID SIDE CHAIN AND IMMUNOASSAY METHODS

[75] Inventors: David L. Brandon, Berkeley; Joseph W. Corse, Lafayette, both of Calif.

[73] Assignee: The United States of America as represented by the Secretary of Agriculture, Washington, D.C.

[21] Appl. No.: 334,069

[22] Filed: Apr. 6, 1989

[51] Int. Cl.$^5$ .................. H01N 43/04; C07G 3/00
[52] U.S. Cl. ........................ 514/25; 514/32; 536/4.1; 536/17.3; 530/350; 530/388.5; 424/88
[58] Field of Search .......... 530/387, 388.5, 350, 530/807; 424/88, 85; 536/4.1, 17.3, 24, 25; 514/37, 42, 43, 45

[56] References Cited

U.S. PATENT DOCUMENTS 4,196,265 4/1980 Koprowski et al. ............ 424/85 X
4,271,145 6/1981 Wands ................................ 424/85

OTHER PUBLICATIONS

D. S. Letham and L. M. S. Palni, *Annual Review of Plant Physiology* 34: 163-197 (1983).
I. M. Scott and R. Horgan, *Planta* 161:345-354 (1984).
J. Badenoch-Jones et al., *Plant Physiology* 75: 1117-1125 (1984).
E. W. Weiler, *Annual Review of Plant Physiology* 35: 85-95 (1984).
E. M. S. MacDonald and R. O. Morris, *Methods in Enzymology* 110: 347-358 (1985).
M. E. Zavala and D. L. Brandon, *Journal of Cell Biology* 97: 1235-1239 (1983).
E. J. Trione and R. O. Morris, *Plant Physiology* 72 (supplement): 114 (1983).
M. L. Woodsworth et al., *Biochemical and Biophysical Research Communications* 114:791-796 (1983).
D. L. Brandon et al., in J. E. Fox and M. Jacobs (eds.) *Molecular Biology of Plant Growth Control*, 209-217, Alan R. Liss, Inc., New York (1987).
A. Williams and I. T. Ibrahim, *Chemical Reviews* 81: 589, 600 (1981).
B. Capon and W. G. Overend, Advances in Carbohydrate Chemistry 15:11, 33-38 (1960).
B. R. Baker and P. M. Tanna, *Journal of the American Chemical Society* 87: 2857-2858 (1965).
R. B. Conrow and S. Bernstein, *Journal of Organic Chemistry* 36:863-870 (1971).
C. C. Duke et al., *Australian Journal of Chemistry* 31: 1291-1301 (1978).
G. Kohler and C. Milstein, *Nature* 256: 495-497 (1975).
G. Kohler and C. Milstein, *European Journal of Immunology* 6: 511-519 (1976).
H. Aigner et al., in W. Voelter et al. (eds.) *Chemistry of Peptides and Proteins*, 209-216, de Gruyter, Berlin (1982).

*Primary Examiner*—C. Warren Ivy
*Assistant Examiner*—Raymond Covington
*Attorney, Agent, or Firm*—M. Howard Silverstein; Joseph A. Lipovsky; Margaret A. Connor

[57] ABSTRACT

Antibodies (polyclonal and monoclonal) having specificity for cytokinins having a glycosylated isoprenoid side chain are described. The antibodies simultaneously recognize a purine ring, an isoprenoid side chain, and a 4'-O-glycoside. The antibodies were elicited using a novel hapten, 9-(2-carboxyethyl) cytokinin-O-glycoside. Immunoassay methods for the determination of cytokinins having a glycosylated isoprenoid side chain which utilize the antibodies are also described.

9 Claims, 6 Drawing Sheets

FIG. 1

FIG. 2 zeatin zeatin-O-glucoside

× zeatin-O-glucoside
◇ g-ribosyl zealtin-O-glucoside
■ zeatin

FIG. 6A
□ zeatin-O-glucoside
× zeatin-g-riboside

FIG. 6B
□ zeatin-O-glucoside
× zeatin-g-riboside

ANTIBODIES TO CYTOKININS HAVING A GLYCOSYLATED ISOPRENOID SIDE CHAIN AND IMMUNOASSAY METHODS

BACKGROUND OF THE INVENTION

1. Field of the invention

The invention relates to and has among its objects the provision of antibodies which are specific for cytokinins having a glycosylated isoprenoid side chain and immunoassay methods for the determination of these cytokinins utilizing the antibodies.

2. Description of the art

Figure 1:
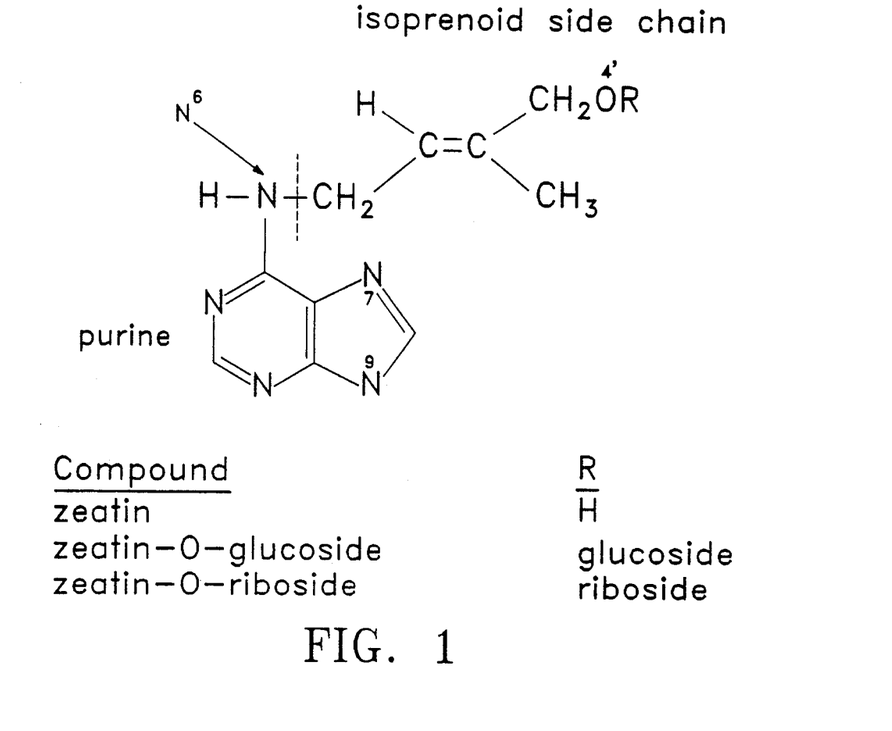
FIG. 1 shows the structures of zeatin (a non-glycosylated cytokinin) and zeatin-O-glucoside and zeatin-O-riboside (cytokinins having a glycosylated isoprenoid side chain).
Figure 2:
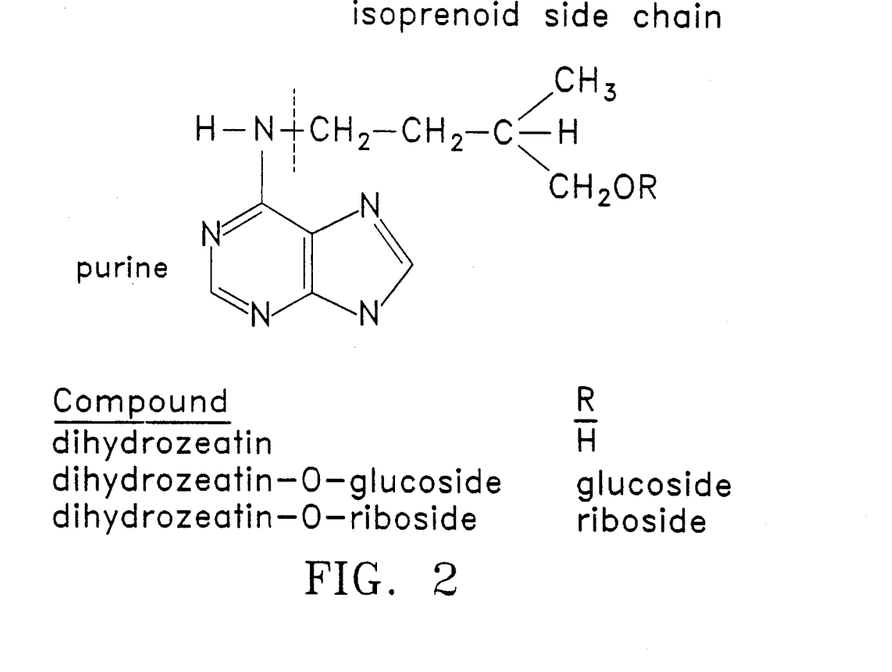
FIG. 2 shows the structures of dihydrozeatin and O-glycosylated derivatives of dihydrozeatin.

Phytohormones regulate many aspects of plant growth and development. Plants, like all higher organisms, senesce, and there is evidence that a complex genetic program for senescence exists and is mediated by the interaction of naturally occurring phytohormones. An important class of phytohormones is the group of cytokinins having a purine ring, hereinafter denoted simply as cytokinins. These compounds are known to evoke a diversity of responses in plants. In addition to occurring in higher plants as free compounds, cytokinins also occur as component nucleotides in tRNA of plants, animals, and microorganisms, and in plant viral RNA (D. S. Letham and L. M. S. Palni, *Annual Review of Plant Physiology* 34: 163–197 (1983). The most important naturally occuring cytokinin is zeatin, shown in FIG. 1. It has a purine moiety (adenine), an isoprenoid side chain (6-(4-hydroxy-3-methylbut-trans-2-enyl), and a hydrogen attached to the 4' oxygen. Another important, naturally occurring cytokinin is dihydrozeatin. As shown in FIG. 2, it differs from zeatin in that the double bond of the isoprenoid side chain (6-(4-hydroxy-3-methylbutyl)) is saturated. Derivatives of zeatin and dihydrozeatin include compounds having a glycoside substituent (e.g., glucose, ribose) linked to the 4' oxygen of the isoprenoid side chain. These compounds are denoted as cytokinins having a glycosylated isoprenoid side chain. Illustrative compounds are shown in FIGS. 1 and 2. Zeatin and dihydrozeatin and their O-glycosylated derivatives can also have N-substitution on the purine ring. Examples include N-glycosides (compounds having a sugar moiety linked to the 7 or 9 nitrogen of the purine ring) or N-amino acyl forms (compounds having an amino acid substituent on the 7 or 9 nitrogen). The N-glycosides may be optionally phosphorylated to mono-, di-, or triphosphate esters.

Figure 3A:
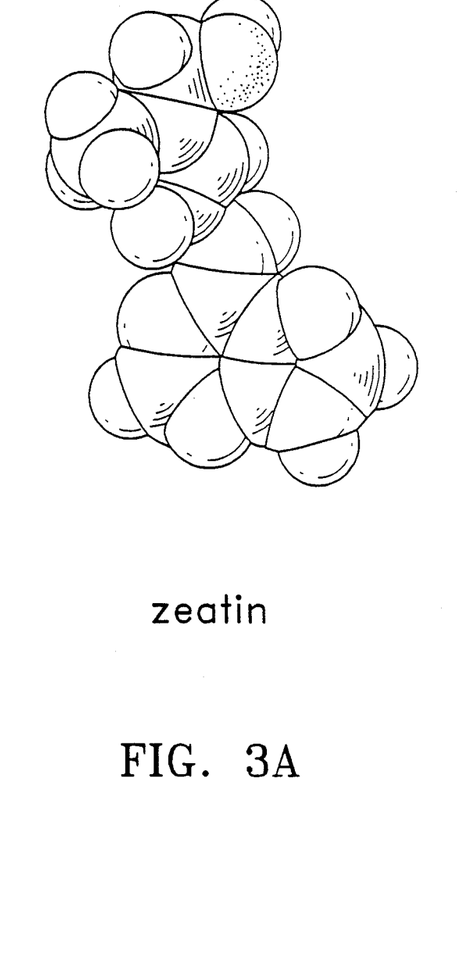
Figure 3B:
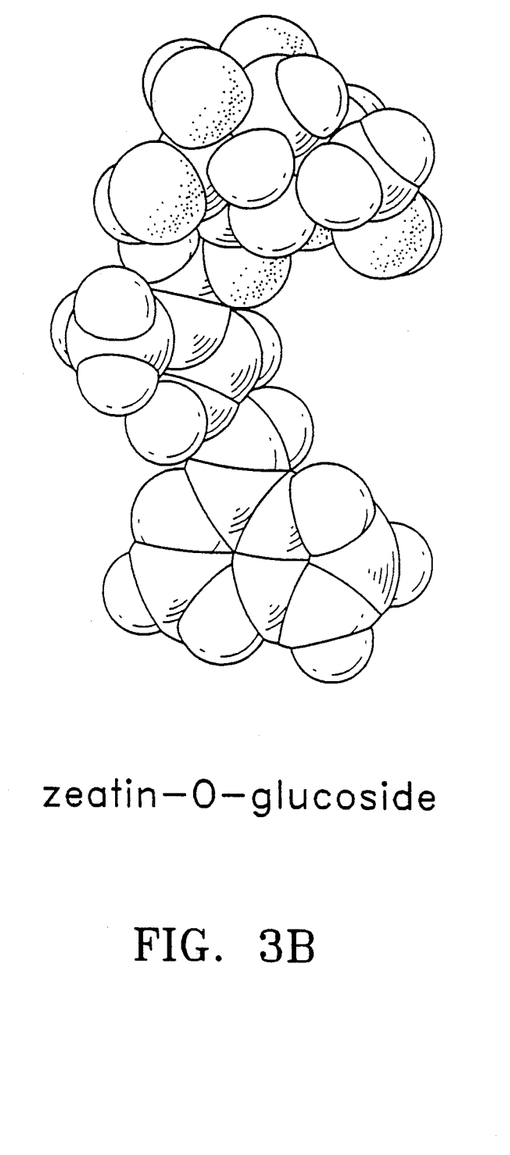

Cytokinins having a glycosylated isoprenoid side chain differ from other cytokinins with regard to stereochemistry, metabolism, and function. The glycosylated side chain is substantially bigger than non-glycosylated side chain (FIG. 3), and the isoprenoid moiety of the side chain is partially masked by the O-glycoside. Thus, the antigenicity of these compounds (that is, their ability to react with receptors of the immune system to trigger antibody formation) differs from the antigenicity of the non-O-glycosides. With regard to differences in metabolism, hydrolysis of cytokinins having a glycosylated isoprenoid side chain is catalyzed by glycosidases which are well documented in the plant literature. In the absence of specific enzymes, these cytokinins can also be hydrolyzed under acidic conditions, especially at elevated temperatures. With regard to function, some studies suggest that cytokinins having a glycosylated isoprenoid side chain function as inactive, storage forms of cytokinins, which can be metabolically activated by enzymatic hydrolysis to the non-O-glycosylated forms.

While the significance of the multiple forms of cytokinins is not fully known, they do not have identical activities in various bioassays. For example, N-ribosides are active in most bioassays, and N-glucosides are inactive in these assays and appear to be dead-end metabolites. Because the different cytokinins do not have the same biological activity, it is important to measure all of the major forms present in a plant or other experimental system (Letham and Palni, 1983, supra). The effective concentration of even a single cytokinin is influenced by the physical sequestration of the molecule within the plant and transport processes which translocate it to different sites. Interconversions of cytokinins in the leaves, for example, could regulate the effective concentration of cytokinins in the chloroplast. The distinct chemical forms appear to have different functions, with ribosides the predominant translocatable form and glucosides the storage forms (Letham and Palni, 1983, supra). Ribotides are also found, sometimes in relatively high concentrations (I. M. Scott and R. Horgan, *Planta* 161: 345–354 (1984) and J. Badenoch-Jones et al., *Plant Physiology* 75: 1117–1125 (1984)).

There are several factors which cause difficulty in the mesurement of cytokinins. One problem is that cytokinins occur in low concentration in plant tissues (nanomolar concentration is typical). Another problem is that, as stated above, they exist in multiple chemical forms in the presence of many other molecules. Further, glycosides and nucleotide forms are inherently unstable to some methods of extraction and concentration. Physicochemical methods of quantitation of cytokinins involve elaborate purification procedures, and utilize complex and expensive instrumentation for detection. While quantitation by such methods is possible, it requires relatively large samples and is labor-intensive and time consuming. Other widely used methods are bioassays, which generally involve cell or organ cultures or growth of whole seedlings. One problem inherent in a bioassay is interference due to the presence of inhibitors of cytokinin activity. A serious problem of the bioassay procedures is that the activity of the multiple forms of cytokinins is not identical from assay to assay. Another problem is that typical bioassays are time consuming (several days) and are not adaptable to automation.

Polyclonal antibodies directed against cytokinins have been reported and have been used for immunoassay (E. W. Weiler, *Annual Review of Plant Physiology* 35: 85–95 (1984)), immunoaffinity fractionation (E. M. S. MacDonald and R. O. Morris, *Methods in Enzymology* 110: 347–358 (1985)), and immunocytochemical localization of cytokinins (M. E. Zavala and D. L. Brandon, *Journal of Cell Biology* 97: 1235–1239 (1983)). Monoclonal antibodies have also been reported which bind to cytokinins, with the first reports being E. J. Trione and R. O. Morris, *Plant Physiology* 72 (supplement): 114 (1983); and M. L. Woodsworth et al., *Biochemical and Biophysical Research Communications* 114: 791–796 (1983). No antibodies have been reported which bind to cytokinins having a glycosylated isoprenoid side chain. Therefore, the immunochemical methods using known antibodies do not permit measurement, fractionation, or localization of this important group of cytokinins. J. Badenoch-Jones et al., supra, first reported that antibodies specific for zeatin and zeatin riboside do not bind efficiently to cytokinins having a glycosylated isoprenoid side chain.

Cytokinins are low molecular weight compounds and are not themselves immunogenic. To obtain an immune response they must be coupled to an immunogenic carrier. Such compounds are known as haptens. In the studies reported by all investigators except D. L. Brandon et al., 1987, discussed infra, the antibodies to cytokinins were elicited using oxidized ribosides as haptens, that is, compounds with reactive aldehyde groups generated by the oxidative cleavage of the 9-N-ribosyl moiety of the corresponding cytokinin riboside. These compounds readily combine with amino groups on a protein carrier, and can then be reduced to form stable amines. These haptens cannot be used to make antibodies to cytokinins having a glycosylated isoprenoid side chain since such reactions would cleave the glycoside and eliminate this important feature of the molecule.

Brandon et al., in J. E. Fox and M. Jacobs (eds.) *Molecular Biology of Plant Growth Control*, 209-217, Alan R. Liss, Inc., New York (1987), used 9-(2-carboxyethyl) zeatin as hapten for eliciting antibodies to zeatin (a nonglycosylated cytokinin). This report does not disclose a hapten suitable for eliciting antibodies to cytokinins with a glycosylated isoprenoid side chain. None of the prior art teaches methods for obtaining such a compound. Cytokinins having a glycoslyated isoprenoid side chain do not have a functional group (other than the glycoside moiety) available for coupling to a carrier. Coupling through the glycoside moiety would destroy the key feature of the molecule in the process of making the immunogenic conjugate. It was unknown whether a suitable functional group could be introduced into a cytokinin having a glycosylated isoprenoid side chain to make a suitable derivative, or hapten, for conjugating to a carrier. The glycoside moiety is labile, and reactions such as hydrolysis, racemization, and oxidation would destroy the hapten.

Even if a functional group could be introduced, there were major uncertainties about the survival of the glycoside moiety during conjugation to carrier. Oxidative reactions or acidic conditions would be likely to hydrolyze the glycoside or cause racemization. Widely used carbodiimide reagents are not appropriate for coupling polyhydroxy compounds (such as cytokinins having a glycosylated isoprenoid side chain) because of side reactions, such as formation of O-alkyl isoureas (A. Williams and I. T. Ibrahim, *Chemical Reviews* 81: 589, 600 (1981) discusses this point as part of a comprehensive review of the reactions of carbodiimides.)

Even if conjugates could be prepared, the prior art does not disclose whether they would be sufficiently stable to reach receptors which trigger antibody production and whether the mouse (or any other species) would recognize it as an antigen and produce antibody. One problem is steric hindrance of the hapten which would alter or prevent antigenicity. Attachment to a protein would sterically hinder part of the hapten and could prevent its interaction with the cells and receptors of the immune system needed to trigger antibody production. The glycoside moiety itself partially masks the isoprenoid side chain (see FIG. 3), which is known to be recognized as an antigen. In view of the foregoing, it could not be predicted whether antibodies could be obtained having the ability to simultaneously recognize a purine ring, an isoprenoid side chain, and a 4'-O-glycoside.

As stated above, understanding how cytokinins regulate the physiological functions of plants necessitates quantitation of all of the forms of cytokinins. In addition, sites of synthesis and action, signals which regulate these processes, and transport phenomena must be characterized. Because of the importance of cytokinin interconversions, these problems must be addressed with analytical methods for cytokinins having a glycosylated isoprenoid side chain. Presently, immunoassays to quantitate these compounds are conducted by measuring zeatin, for example, before and after treatment with a glycosidase which hydrolyzes the glycosidic bond. Obtaining the measurement indirectly as the difference between two assay results is inherently less precise than performing a direct measurement. In addition, antibodies specific for cytokinins having a glycosylated isoprenoid side chain would provide ideal analytical tools to measure the enzymes which synthesize or degrade these cytokinins and growth regulatory substances which modulate the activity of these enzymes. Antibodies specific for cytokinins having a glycosylated isoprenoid side chain would provide the ideal reagents for these immunochemical methods.

SUMMARY OF THE INVENTION

The invention comprises antibodies (polyclonal and monoclonal) having specificity for cytokinins having a glycosylated isoprenoid side chain. The antibodies of the invention are able to simultaneously recognize three key features: (1) a purine ring, (2) an isoprenoid side chain, and (3) a 4'-O-glycoside.

The antibodies were elicited using a novel hapten, 9-(2-carboxyethyl) cytokinin-O-glycoside. This is the first report of the synthesis of a 9-carboxyethyl cytokinin having a glycosylated side chain.

Another aspect of the invention is the provision of antibodies to cytokinins having a glycosylated isoprenoid side chain which have one or more of the following specialized characteristics: (1) they bind to cytokinins having a glucosylated side chain; (2) they bind to zeatin-O-glucoside; and (3) they bind to cytokinins having a glycosylated isoprenoid side chain having substitution on the purine ring (e.g., N-glycosides, including ribosides and ribotides).

Another aspect of the invention is the provision of screening methods to obtain antibodies to cytokinins having a glycosylated isoprenoid side chain having the aforementioned characteristics.

Still another aspect of the invention is the provision of immunoassay methods for the determination of cytokinins having a glycosylated isoprenoid side chain which utilize the antibodies described above.

Another aspect of this invention is to provide antibodies for immunoaffinity separation of cytokinins having a glycosylated isoprenoid side chain from nonglycosylated forms and other compounds.

Another aspect of the invention is to provide kits for the assay of cytokinins having a glycosylated isoprenoid side chain.

Another aspect of the invention is to provide kits for analysis of cytokinins by using the antibodies of the invention together with antibodies specific for other cytokinins.

In summary, this invention provides antibodies to cytokinins having a glycosylated isoprenoid side chain as a means for (1) accurately and rapidly measuring low levels of these compounds such as are present in extracts of plant tissues; (2) specifically measuring cytokinins having a glycosylated isoprenoid side chain in the presence of other cytokinins; (3) monitoring changes in the ratio of O-glycosylated and non-O-glycosylated cytokinins which may reflect responses to aging and stress; (4) accurately determining the levels and sites of localization of cytokinins having a glycosylated isoprenoid side chain in plant tissues; (5) separating cytokinins having a glycosylated isoprenoid side chain from other cytokinins, facilitating analysis by immunochemical or physicochemical techniques.

In accordance with this discovery, it is an object of the invention to provide antibodies with specificity for cytokinins having a glycosylated isoprenoid side chain and methods of using the antibodies for facile and accurate measurement of these phytohormones.

Another object of the invention is to provide immunoassay methods for measurement of very low levels of cytokinins having a glycosylated isoprenoid side chain in plant tissues.

It is still a further object to provide methods for studying receptors and enzymes which bind, synthesize, or metabolize cytokinins having a glycosylated isoprenoid side chain.

Still another object of the invention is to provide kits useful for the assay of cytokinins having a glycosylated isoprenoid side chain.

A further object of the invention is to provide a method for purifying cytokinins having a glycosylated isoprenoid side chain or for specifically removing these components from a mixture of compounds.

Other objects and advantages of this invention will become readily apparent from the ensuing description.

BRIEF DESCRIPTION OF THE DRAWINGS

FIG. 3 shows space-filling models of E-zeatin (FIG. 3A) and E-zeatin-O-$\beta$-D-glucopyranoside (FIG. 3B).

FIG. 6 shows standard curves for E-zeatin-9-riboside and E-zeatin-O-$\beta$-D-glucopyranoside measured simultaneously using monoclonal antibodies 94 (FIG. 6A) and ATCC HB 9658 (FIG. 6B).

FIG. 7 shows logit-transformed data for ELISA of corn root tip E-zeatin (FIG. 7A) and E-zeatin-O-$\beta$-D-glucopyranoside (FIG. 7B).

DETAILED DESCRIPTION OF THE INVENTION

The invention comprises antibodies (polyclonal and monoclonal) which are specific for cytokinins having a glycosylated isoprenoid side chain. For purposes of this invention, the expression "cytokinins having a glycosylated isoprenoid side chain" and the equivalent expression, "cytokinin-O-glycoside," are defined to mean derivatives of 6-aminopurine with a glycosylated isoprenoid moiety substituted at the $N^6$ position. Examples of such cytokinins include compounds such as zeatin-O-glucoside, zeatin-O-riboside, dihydrozeatin-O-glucoside, dihydrozeatin-O-riboside as well as compounds having further substitution on the purine ring. Antibodies specific for cytokinins having a glycosylated isoprenoid side chain are defined as antibodies which simultaneously recognize a purine ring, an isoprenoid side chain, and a 4'-O-glycoside.

The antibodies have the ability to distinguish between cytokinins having a glycosylated isoprenoid side chain and cytokinins which lack a glycosylated isoprenoid side chain, that is, they bind with at least 100-fold greater affinity to the O-glycoside form. For purposes of this invention, the expression "cytokinins lacking a glycosylated isoprenoid side chain" and the equivalent expression, "non-O-glycosylated cytokinins," are defined to mean derivatives of 6-aminopurine with an non-glycosylated isoprenoid moiety substituted at the $N^6$ position. Examples of such cytokinins include isopentenyladenine, zeatin, and dihydrozeatin, as well as compounds having further substitution on the purine ring.

Another embodiment of the invention comprises antibodies which specifically bind to cytokinins having a glucosylated side chain. In another embodiment, the antibodies specifically bind to zeatin-O-glucoside. Still another embodiment includes antibodies which bind to cytokinins having a glycosylated isoprenoid side chain and having one or more substituents in the 7- and 9-positions.

Methods.

Preparation of hapten.

9-(2-carboxyethyl) cytokinin-O-glycoside was used as the hapten to prepare the antibodies of the invention. The synthesis of the 9-(2-carboxyethyl) cytokinin-O-glycoside had substantial problems not encountered with synthesis of cytokinin-O-glycosides or 9-(2-carboxyethyl) cytokinins which are not glycosylated. One reason was the chemical instability of the glucose moiety. During the synthesis of the hapten and attachment to protein, it was critical to find conditions which would minimize hydrolysis, racemization, and oxidation which would destroy the hapten. Another problem was the presence of the carboxylic acid group attached to the purine ring. Acids are known to labilize glycosidic linkages (B. Capon and W. G. Overend, *Advances in Carbohydrate Chemistry* 15:11–51 (1960)). Further, presence of an acid also favors production of unwanted glycoside esters. Thus, the practical success of a synthesis to produce both desired features of the hapten-a 9-(2-carboxyethyl) group and an intact glycosylated isoprenoid side chain-was uncertain.

Attachment of the hapten to protein for eliciting antibodies presented additional difficulties. Conventional carbodiimide reagents are unsuitable for coupling polyhydroxy acids (such as 9-(2-carboxyethyl) cytokinin-O-glycosides) because of side reactions, such as formation of O-alkyl isoureas (A. Williams and I. T. Ibrahim, 1981, supra). We found 2-morpholinoethylisocyanide suitable for conjugation of 9-(2-carboxyethyl) cytokinin-O-glycosides to proteins for use as immunogens and enzyme-labeled ligands in ELISA. The resulting products were remarkable for their efficacy as immunogens and labeled ligands in ELISA, with excellent enzymatic activity and stability during storage and premitting sensitive and specific immunoassay of cytokinin-O-glycosides.

The specific steps of preparation of hapten are as follows.

The first step in the preparation of 9-(2-carboxyethyl)cytokinin-O-glycosides is preparation of a 6-substituted-9-(2-carbomethoxyethyl)purine. Acceptable 6-substituents are chloro and thiomethyl groups. The reaction proceeds by a base-catalyzed Michael addition of methyl acrylate to the 6-substituted purine. The chloro substituent is preferred because high yield is obtained under mild conditions. A mixture of 6-substituted purine, methyl acrylate, and finely ground potassium carbonate (1:5:0.06 molar ratio preferred) is stirred in a moderately polar organic solvent such as dimethylsulfoxide (DMSO) at room temperature for at least 20 hours, with 48 hours preferred. The resulting ester, 6-substituted-9-(2-carbomethoxyethyl)purine, is saponified with dilute base. Acidification of the reaction mixture yields 6-substituted-9-(2-carboxyethyl)purine.

The glycosylated side chain is preferably assembled, using a phthaloyl group to block the amino group and acetyl groups to protect the glycoside moiety. The appropriate isoprenoid derivative, for example, E-2-methyl-4-phthalimidobut-2-enyl-2,3,4,6-tetra O-acetyl-glycoside, is prepared by a suitable method, for example, by the general procedure of glucuronide formation of R. B. Conrow and S. Bernstein, *Journal of Organic Chemistry* 36: 863–870 (1971). The O-acetyl groups are hydrolytically removed with macroporous anionic exchanger (hydroxyl form) prepared in methanol (L. A. Reed et al., *Journal of the Chemical Society, Chemical Communications*: 760–761, 1981). The catalyst is removed by filtration, the volatiles removed in vacuo, and the residue recrystallized from methanol-ethyl ether. The phthalimide is then hydrolyzed, and the phthalide removed. The resulting amine is reacted with the 9-(2-carboxyethyl)-6-substituted purine using 1-butanol as solvent and a proton sink. The selection of an appropriate base as a proton sink is important to achieve a high yield of the desired product. It must be sufficiently long to be sterically hindered so as not to react with the 6-substituted purine, and it must be volatile under reduced pressure so as to be readily removed. Examples are tertiary amines derived from ethylamine, with N,N-diisopropylethylamine preferred. The 9-(2-carboxyethyl) cytokinin is isolated by a suitable method, for example, by adjusting the cold, concentrated aqueous solution of the reaction mixture (after removal of the butanol and amine in vacuo) to a pH of 4.0–4.2. The cytokinin derivatives are purified, for example by chromatography on silica using appropriate ethyl acetate-methanol gradients.

The synthesis of hapten is shown below wherein the synthesis of 9-(2-carboxyethyl)zeatin-O-glucoside is illustrated.

2-Methyl-4-phthalimidobut-2-enyl-glucoside 9-(2-Carboxyethyl)zeatin-O-glucoside

Preparation of protein conjugates. 9-(2-carboxyethyl) cytokinin-O-glycosides may be conjugated to an immunogenic carrier such as protein or polysaccharide by any means known to the art. The preferred method is to couple the carboxyl group to an available amino group of bovine serum albumin (BSA). The coupling reagent of choice is 2-morpholino-ethylisocyanide so as to avoid possible formation of O-alkyl isourea compounds. Preferred conditions are as follows. The 9-(2-carboxyethyl) cytokinin is dissolved in a polar organic solvent such as dimethylformamide (DMF): dimethylsulfoxide (DMSO) (3:1), and an equimolar amount of a catalyst such as N-hydroxysuccinimide in DMF and 20% molar excess of the 2-morpholino-ethylisocyanide are added. The mixture is stirred, preferably in absence of light, at room temperature for about 30 min. An equimolar amount of a base such as dimethylaminopyridine in DMF is then added to the mixture, followed by dropwise addition, with continuous stirring, of an aqueous solution of the protein to be coupled. BSA at a concentration of 2 mg/mL is a typical such solution, but other proteins and enzymes in the range of 1–5 mg/mL are suitable. After continued incubation in the dark (several hours or overnight), the coupled protein is purified by any technique known to the art, with dialysis against buffered saline preferred for its simplicity.

Immunization. The immunizing preparation consists of a protein mixture including derivatized cytokinin having a glycosylated isoprenoid side chain conjugated to an immunogenic carrier. It may contain other proteins, or-preferred-it may be a homogeneous, pure preparation of 9-(2-carboxyethyl) cytokinin-O-glycoside conjugated to a protein such as BSA. Optionally, the protein mixture may be treated in various ways or combined with adjuvants to enhance the immune response.

The choice of animal for immunization to obtain polyclonal antibodies depends mainly on the quantity of serum which will be needed. Mice, rats, rabbits, and goats are acceptable, with rabbits preferred for ease of handling. For production of monoclonal antibodies, the choice of animal for immunization is limited by the availability of the fusion partner-the permanent plasmacytoma cell line, and mouse, rat, and human hybridomas have been prepared by many investigators. Mice are preferred because of ease of handling. In addition, for monoclonal antibody production, the generation of an immune response can be performed in vitro.

Inoculations of the animal can be by various routes (intraperitoneal or subcutaneous, preferred). A series of inoculations, generally at three week intervals, with an immunogen such as a protein conjugate of cytokinin having a glycosylated isoprenoid side chain emulsified in complete Freund's adjuvant, elicits good antibody response after two to three inoculations. A suggested inoculum is 10–100 μg of conjugate emulsified in complete Freund's adjuvant for mice, and 0.1–1 mg of emulsified conjugate for rabbits or larger animals. Other routes and immunization schedules and other adjuvants or no adjuvant are alternatives.

Screening Sera of Inoculated Animals for Antibodies Which Bind to Cytokinins Having a Glycosylated Isoprenoid Side Chain.

The presence of antibodies to cytokinins having a glycosylated side chain are determined preferably by ELISA. Sera are selected which have significant, specific binding to a solid phase containing protein conjugate of cytokinin having a glycosylated side chain at a dilution factor of at least 1000. Inoculations are continued at three-week intervals until this acceptable titer is achieved.

Antibodies can be used in the form of sera or after purification by any technique known to the art, for example fractionation with ammonium sulfate, chromatography on ion exchange resin, and immunoaffinity chromatography using 9-(2-carboxyethyl) cytokinin having a glycosylated side chain as immobilized ligand. Antibodies are stored frozen or are refrigerated in the presence of an anti-microbial agent such as 0.02% sodium azide.

Uses of Polyclonal Antibodies. The polyclonal antibodies of the invention have the unique feature of being specific for cytokinins having glycosylated isoprenoid side chain. No equivalent specificity has been reported in the literature. They can be used for ELISA analysis of cytokinins by immunoassay (details discussed infra), or can be coupled to a solid support (for example, agarose) to form a matrix for immunoaffinity fractionation of cytokinins.

Preparation of Hybridoma Cell Lines.

Preparation of hybridoma cell lines can be done by techniques which are well known to those who are skilled in the art. (See, for example, G. Kohler and C. Milstein, *Nature* 256:495–497 (1975); *European Journal of Immunology* 6: 511–519 (1076); Koprowski et al., U.S. Pat. No. 4,196,265, and Wands, U.S. Pat. No. 4,271,145, all of which are herein incorporated by reference.)

The choice of cell line as fusion partner can influence the results, including frequency of cell fusions and growth characteristics of the resulting hybridoma. However, many cell lines are widely available. Exemplary of two cell lines are P3-NS1-1-Ag4-1 and the closely related P3X63-Ag8.653.

Production of Hybrid Cells. Cell fusion techniques, selection procedures, and methods for growth of hybridomas are known to those skilled in the art. In one effective cell fusion procedure, poly(ethyleneglycol) is used in the fusion step, and hypoxanthine-aminopterin-thymidine is used in the selective medium.

Analysis of Hybridomas. The growing colonies are tested for the presence of antibodies that bind the cytokinin having a glycosylated isoprenoid side chain. Detection of hybridoma antibodies can be performed with a variety of assays. We have found that one way is to attach a protein conjugate of 9-(2-carboxyethyl) cytokinin-O-glycoside to the surface of assay wells in a multiwell microtitration plate made of polystyrene or polyvinylchloride and widely available commercially. Standard assay methodology and widely used commercial reagents, such as rabbit anti-mouse immunoglobulin G (IgG) antibodies attached to horseradish peroxidase (HRP), can be used to reveal the presence of antibodies in the culture supernatants.

Cloning of Hybridomas. Cloning of hybridomas which are positive for desired antibody production can be carried out as soon as they are detected by any method known to the art, or after further screening as described below. In the preferred embodiment, cloning is accomplished by limiting dilution in liquid medium. The cloning procedure can be repeated to increase the probability of clonality. Antibody-secreting hybridomas can be grown in a variety of vessels, in devices such as hollow fibers, or within a host animal.

Screening of Clones. To obtain the monoclonal antibodies of the invention, screening is carried out as follows:

Preliminary Screening. Supernatant culture fluid from the cloned hybridomas of interest is optionally submitted to a preliminary screening to confirm the presence of antibodies that bind cytokinin having a glycosylated isoprenoid side chain. We have found that the direct binding assay (or titration), as described above, is a convenient and efficient technique for the preliminary screening step.

Screening of Antibodies Which are Specific for Cytokinins Having a Glycosylated Isoprenoid Side Chain.

Supernatant culture fluid from the cloned hybridomas of interest is screened to select antibodies having an affinity constant of at least $5 \times 10^6 \text{ M}^{-1}$. Affinity can be measured by any technique known in the art for example, inhibition ELISA, equilibrium dialysis using labeled cytokinin-O-glycoside, or radioimmunoassay (RIA). Where the contemplated use of the antibody is in an ELISA assay, inhibition ELISA is the screening technique of choice. In ELISA, the affinity constant is defined as the reciprocal of the concentration of analyte resulting in half-maximal binding of the labeled ligand to the solid phase ($I_{50}$). Inhibition ELISA is conducted at a final antibody concentration (i.e., dilution from tissue culture supernatant) to give 50 to 100% of maximal binding to an assay well coated with protein conjugate of cytokinin having a glycosylated isoprenoid side chain. Antibody is mixed with a range of concentrations of the cytokinin having a glycosylated isoprenoid side chain, incubated, and applied to the assay plate. The plate is then incubated, washed, and developed as for the direct binding assay. Antibodies are selected which have an $I_{50}$ of less than $2 \times 10^{-7}$ M, equivalent to an affinity constant of at least $5 \times 10^6$ M$^{-1}$.

The antibodies selected as described above are further tested for binding to a second solid phase coated with a protein conjugate of cytokinin lacking a glycosylated isoprenoid side chain, either through the activated aldehyde groups of the oxidized 9-riboside form of the cytokinin or through the 9-(2-carboxyethyl) group of the 9-(2-carboxyethyl) cytokinin. A one hundred-fold greater affinity for the solid phase containing the O-glycoside is a quick method to estimate the relative affinity, which can be measured more precisely by any technique known in the art for example, inhibition ELISA, equilibrium dialysis using labeled cytokinins, or radioimmunoassay. Where the contemplated use of the antibody is in an ELISA assay, inhibition ELISA is the screening technique of choice. Inhibition ELISA is conducted as described above. Antibodies are selected which have an $I_{50}$ for cytokinin lacking a glycosylated isoprenoid side chain at least 100-fold higher than the $I_{50}$ for cytokinin having a glycosylated isoprenoid side chain.

Supernatant culture fluid from the cloned hybridomas of interest containing antibodies which bind cytokinin having a glycosylated isoprenoid side chain are optionally screened for other specificities as described below.

Screening for antibodies which bind to cytokinins with a glucosylated isoprenoid side chain is performed as described above, wherein the 4'-O-glycoside moiety is glucose.

Screening for antibodies which bind zeatin-O-glucoside is performed as described above, wherein the cytokinin having a glycosylated isoprenoid side chain is zeatin-O-glucoside and the cytokinin is zeatin.

Screening for Antibodies which bind cytokinins having a glycosylated isoprenoid side chain, with further substitution on the purine ring comprises further screening, preferably by inhibition ELISA, for their ability to bind cytokinins with further substitution on the purine ring. Antibodies are selected for which the affinity constant for binding to the further substituted derivatives is no more than 10-fold lower than the affinity constant for the unsubstituted compound.

After screening additional quantities of the selected antibodies may be prepared by growing hybridomas secreting the antibodies in vitro or in vivo by methods known in the art. The antibodies are isolated by known techniques.

The monoclonal antibodies of the invention possess several unique features. They are specific for cytokinins having a glycosylated isoprenoid side chain. They are of sufficiently high affinity to make them suitable for a wide variety of immunoassays. Binding can be achieved in the range of $10^{-9}$ to $10^{-6}$M, suitable for analysis of cytokinins in plant extracts. Antibodies which bind cytokinins having a glycosylated isoprenoid side chain can be obtained which do not bind the purine form or N-glycosylated purine form of the cytokinin. No equivalent specificity or sensitivity of analytical immunochemical methods has yet been reported in the literature, and this range of sensitivity is close to that achieved by physicochemical methods requiring extensive sample preparation and complex and expensive instruments.

The monoclonal antibodies can bind to cytokinins having a glycosylated isoprenoid side chain which has been labeled with a molecule such as HRP. The ability of the antibodies of the invention to bind to cytokinin having a glycosylated isoprenoid side chain after labeling with a large molecule such as HRP enables a variety of convenient labeled forms to be used in immunochemical methods. The antibodies of the invention can be attached to a solid phase, such as polystyrene, with retention of activity. This means that the antibodies could be used for affinity purification of cytokinins having a glycosylated isoprenoid side chains as well as for ELISA formats using immobilized antibodies.

Hybridomas which produce and secrete monoclonal antibodies to cytokinins having a glycosylated isoprenoid side chain were prepared as described above. Representative of these is clone 240 which produces and secretes antibodies that bind to E-zeatin-O-$\beta$-D-glucopyranoside and do not bind to zeatin, 9-ribosylzeatin, or zeatin-9-$\beta$-D-glycopyranoside. Clone 240 has been deposited in the American Type Culture Collection, Rockville, Md, with the accession number ATCC HB 9658.

Uses of Antibodies of the Invention.

Measurement of cytokinins having a glycosylated isoprenoid side chain. The measurement of cytokinins having a glycosylated isoprenoid side chain is carried out using the antibodies of the invention. The preferred method is use of ELISA.

Inhibition ELISA. In this assay, a sample to be analyzed is incubated with antibody specific for cytokinins having a glycosylated isoprenoid side chain. Portions of this mixture are transferred to any solid phase, such as wells of an assay plate, a bead, or a solid-state electronic device, coated with the cytokinins having a glycosylated isoprenoid side chain (e.g., a protein conjugate of 9-(2-carboxyethyl) cytokinin having a glycosylated isoprenoid side chain). After an incubation (one hour preferred), the solid phase is drained, washed, and rinsed, and bound antibody is detected. The preferred method of detection on an assay plate or bead is use of an enzyme-labeled second antibody recognizing the first antibody. HRP and it substrate, 2,2'-azinobis-3-ethylbenzthiazolinesulfonic acid (ABTS), are preferred reagents for labeling and measuring bound antibodies. The immunoassay can be performed using other labels, such as radiolabels or chromophores, or with directly labeled antibody. If an electronic device is used as solid phase, an appropriate electronic detector is used.

A standard curve relating the amount of bound antibody to concentration of cytokinin having a glycosylated isoprenoid side chain is constructed from assays using authentic cytokinin having an isoprenoid side chain as analyte. The concentration of cytokinin having a glycosylated isoprenoid side chain in the sample is determined by reference to the standard curve.

Competition ELISA. In this variation of the assay, monoclonal antibody specific for cytokinin having a glycosylated isoprenoid side chain is attached to a solid phase, with multiwell plastic microtitration plates the preferred embodiment. Covalent attachment to a surface, bead, solid-state electronic device or relatively nonspecific adsorption to such surfaces may be employed. Sample to be analyzed is mixed with an appropriate amount of labeled cytokinin having a glycosylated isoprenoid side chain, which can be labeled with HRP, or other labels such as chromophores, radiolabels, paramagnetic labels, enzymes, and the like. The mixture of labeled cytokinin having a glycosylated isoprenoid side chain and analyte is applied to the solid phase, and after incubation (one hour preferred), the solid phase is drained, washed and rinsed, and bound labeled cytokinin having a glycosylated isoprenoid side chain is determined by a method dependent on the surface and label used. In a preferred embodiment, HRP conjugated with 9-(2-carboxyethyl) cytokinin having a glycosylated isoprenoid side chain is visualized with ABTS as substrate. The amount of cytokinin having a glycosylated isoprenoid side chain in the sample is determined with reference to a standard curve, as described above.

Applicability of Techniques.

The choice of particular technique and reagents depends on the particular application, since simplicity and cost (among other parameters) vary. But anyone skilled in the art could apply the generalized techniques.

These procedures for analysis of samples containing cytokinins having a glycosylated isoprenoid side chains can be readily automated, for example by provision of automatic pipeting equipment and automated ELISA reader and computer. The invention can also be adapted to a variety of kits, in which antibody, suitably labeled cytokinin having a glycosylated isoprenoid side chain, or anti-immunoglobulin, substrate, and standards are supplied in separate containers, or, as appropriate, coated on solid phases. The surface could be a plastic assay dish, a bead, or electronic solid-state transducer that would permit real-time monitoring, for example. Reagents may be provided in solid or liquid form. The assay could also be arranged as a qualitative assay-such as might be used in a quality control application. In such a format, the appropriate reagents would be coated on surfaces and supplied in solutions at concentrations which would reveal a positive assay if more than a predetermined minimum of cytokinin having a glycosylated isoprenoid side chain were present in the sample. Such a kit could include materials for assay of other cytokinins and thus comprise a method for determination of the major cytokinins in a plant-derived sample. Similar procedures can be used to measure enzymatic formation of cytokinin having a glycosylated isoprenoid side chain or enzymatic hydrolysis of the glycosylated isoprenoid side chain.

The sample can consist of any plant tissue or extract, or any tissue or extract derived from a plant or organism synthesizing a purine derivative similar to cytokinin having a glycosylated isoprenoid side chain or possessing enzymes which synthesize or degrade cytokinin having a glycosylated isoprenoid side chains.

The ELISA methods could be applied in several ways. (a) Plant tissues or fluids could be analyzed for cytokinin having a glycosylated isoprenoid side chain by ELISA following extraction. (b) Plant tissues or cells could be analyzed for cytokinin having a glycosylated isoprenoid side chain binding sites by immunohistochemical techniques. (c) The ELISA could be used to detect the product of genes coding for sugar transferases which synthesize cytokinin having a glycosylated isoprenoid side chain or glycosidases which hydrolyze cytokinin having a glycosylated isoprenoid side chain. (d) The antibody could be used for affinity purification of cytokinin having a glycosylated isoprenoid side chain or for removal of cytokinins having a glycosylated isoprenoid side chain from a sample.

EXAMPLES

The following examples are intended only to further illustrate the invention and are not intended to limit the scope of the invention which is described by the claims.

EXAMPLE 1

This example describes the synthesis of the hapten, E-9-(2-carboxyethyl)zeatin-O-$\beta$-D-glucopyranoside.

6-Chloro-9-(2-carbomethoxyethyl)purine. A mixture of 4.64 g (0.03 mol) of 6-chloropurine, 12.9 g (0.15 mol) of methyl acrylate, 0.3 g (0.002 mol) of finely ground potassium carbonate and 50 mL of dimethylsulfoxide was stirred at room temperature for 48 h. The solvent was removed by distillation (0.1 mm) and the residue was extracted with methanol. The insoluble salts were removed by filtration and the filtrate was concentrated in vacuo. The residue was then dissolved in methanol, and petroleum ether was added to effect crystallization. Yield 3.71 g (51%); m.p. 93.5°.

6-Chloro-9-(2-carboxyethyl)purine. A solution of 10.4 g (0.0432 mol) of 6-chloro-9-(2-carbomethoxyethyl)purine in 400 mL dioxane, 20 mL $H_2O$ and 50 mL N NaOH was stirred 2 h at room temperature. Nearly all the solvent was removed by roto-evaporation and 50 mL of N HCl was added. The mixture was chilled and the precipitate collected; 9.00 g (92%); recrystallized from methanol-petroleum ether; mp 163°-165°; $^1$H NMR (200 MHz, DMSO-$d_6$) $\delta$8.80 (1H, s, 7 or 8-H), 4.52(2H, t), 2.97 (2H, t, $CH_2CO$).

E-2-Methyl-4-phthalimidobut-2-enyl 2,3,4,6-tetra O-acetyl-$\beta$-D-glucopyranoside. The general procedure of glucuronide formation of R. B. Conrow and S. Bernstein, 1971, supra, was followed. A mixture of 11 g (0.048 mol) of E-2-methyl-4-phthalimidobut-2-enol (mp 104°-105°, J. Corse and J. Kuhnle, *Synthesis* 618-619 (1972) and 17.2 g of $CdCO_3$ (Johnson and Matthey, Seabrook, N. H.) in 1200 mL of toluene was dried by distilling about 200 mL of toluene from the flask (stirring). A solution of 39.7 g (0.1 mol) of 2,3,4,6-tetra-O-acetyl-$\alpha$-glucopyranosyl bromide (acetobromoglucose) in 200 mL of dry toluene was added to the stirred, refluxing mixture over 1 h. The hot mixture was filtered through a Celite pad and the toluene was removed in vacuo from the filtrate. The resulting tan gum (46 g) contained the desired product, starting alcohol and its acetate. Purification was simplified by acetylating the entire mixture with 50 mL of acetic anhydride, 135 mL of pyridine and 1 g of 4-dimethylaminopyridine (steam bath, ½ h). The volatiles were removed in vacuo and the residue was dissolved in ethyl acetate and the solution washed with $H_2O$, dilute HCl, $KHCO_3$ solution and $H_2O$. After drying and removal of the solvent, 29.8 g remained, which was divided into 4 portions and chromatographed on silica (J. T. Baker, flash chromatography grade, 40 $\mu$m, 50 cm×4 cm column, hexane:ethyl acetate (65:35); yield 14.36 g (53.3%); mp 118°-120°; $^1$H NMR identical to that reported by C. C. Duke et al., *Australian Journal of Chemistry* 31: 1291-1301 (1978).

E-2-Methyl-4-phthalimidobut-2-enyl-$\beta$-D-glucopyranoside. A solution of 4 g of E-2-methyl-4-phthalimidobut-2-enyl 2,3,4,6-tetra-O-acetyl-$\beta$-D-glucopyranoside in 500 mL methanol was stirred 16 h with 5 g Amberlyst A-26 (OH) prepared in methanol (L. A. Reed et al., 1981, supra). The catalyst was removed by filtration, the volatiles removed in vacuo and the residue recrystallized from methanol-diethylether; yield 2.27 g (74%); mp 143°-145°; m/z (chemical ionization using NH$_3$) 411.1745 (calculated for C$_{19}$H$_{27}$N$_2$O$_8$;411.1767); $^1$H NMR (200 MHz, DMSO-d$_6$) δ 7.86 (4H, m, Ar), 5.50 (1H, t, C=CH), 5.03 (1H, d, glucose OH), 4.96 (2H, m, glucose OH), 4.46 (2H, t, CH$_2$N), 4.22 (2H, dd, CH$_2$OH, J=28). 4.12 (1H, anomeric H, J=8), 3.63 (1H, q, glucose OH), 2.8–3.4 (4H, m, glucose H), 1.78 (3H, s, CH$_3$).

E-9-(2-carboxyethyl)-O-β-D-glucopyranosylzeatin.

E-2-methyl-4-phthalimidobut-2-enyl-β-D-glucopyranoside (1.17 g; (3 mmol) dissolved in a mixture of 26.9 mL 2-propanol and 4.54 mL H$_2$O was stirred overnight with 0.57 g of sodium borohydride (J. O. Osby et al., *Tetrahedron Letters* 25:2093–2096 (1984)). Glacial acetic acid (3.14 mL) was added and the solution heated 2 h at 80° and then evaporated to dryness in vacuo. The dry residue was triturated several times with 5 mL portions of ether to remove phthalide. The remainder was heated 10 h at 100°–105° with 0.6 g of 6-chloro-9-(2-carboxyethyl)purine, 20 mL of 1-butanol and 2 mL of N,N-diisopropylethylamine. The volatiles were removed in vacuo and the residue dissolved in 4.5 mL of DMSO and the filtered solution applied to a 21.4 mm × 50 cm HPLC column (C-18, 8 micron). Elution was carried out with CH$_3$CN:H$_2$O (6:94); yield 0.199 g (14.6%); mp 195°–198° (dec) with sintering at 165°; m/e 453.1839 (calculated for C$_{19}$H$_{27}$N$_5$O$_8$: 453.1758; $^1$H NMR (200 MHz, DMSO-d$_6$+D$_2$O) δ8.20 (1H, s, 7 or 8-H), 8.03 (1H, s, 7 or 8-H), 7.38 (1H t, NH), 5.62 (1H, t, =CH), 4.36 (2H, t, NCH$_2$C), 4.21 (2H, d, NCH$_2$C=), 4.14 (H, d, anomeric H), 4.02 (2H,dd, J=25, CH$_2$O), 3.54 (2H, q,glucose H), 2.9–3.3 (3H, cmplx, glucose H), 2.85 (2H, t, CH$_2$CO$_2$),1.73 (3H, s, CH$_3$).

EXAMPLE 2

This example describes production of antibodies which bind E-zeatin-O-β-D-glucopyranoside.

Chemicals.

N$^6$-2-isopentenyladenine and its riboside were synthesized by the method of R. H. Hall and M. J. Robin, in W. W. Zorbach and R. S. Tipson (eds.) *Synthetic Procedures in Nucleic Acid Chemistry*, vol. 1, Interscience Publishers, New York (1968). Zeatin and its riboside were synthesized as described by J. A. Kuhnle et al., *Physiologia Plantarum* 41: 14–21 (1977). (RS)-dihydrozeatin and its riboside were synthesized essentially as described by J. Corse et al., *Journal of Plant Growth Regulation* 2: 47–57 (1983). Zeatin-9-glucoside was synthesized according to I. M. Scott et al., *Planta* 149: 472–475 (1980). 9-(2-carboxyethyl)zeatin-O-glucoside was synthesized as described above in Example 1. Zeatin-O-glucoside and its 9-riboside were synthesized as described for the 9-(2-carboxyethyl) derivative except that 6-chloropurine and its 9-riboside were used instead of 9-carboxyethyl-6-chloropurine. All compounds were purified by high performance liquid chromatography. Purity and structural identity were determined by elemental analysis, melting point determination, and by proton nuclear magnetic resonance. Magnetic resonance spectra were measured at room temperature on either a Varian EM 390 (90 MHz) or a Nicolet NMC-200 (200 MHz) spectrometer.

Cytokinin ribotides and the O-glucosides of (RS)-dihydrozeatin and (RS)-dihydrozeatin riboside were obtained from Apex Organics (Oxford, U. K.). Other purines and ribosides were obtained from Sigma Chemical Co. (St. Louis, MO).

Preparation of Conjugates using Oxidized Ribosides.

Conjugation of cytokinin ribosides to BSA and other proteins was performed according to B. F. Erlanger and S. M. Beiser, *Proceedings of the National Academy of Sciences USA* 52: 68–74 (1964). These conjugates contained 10 to 20 mol cytokinin per 100,000 g protein. Conditions were modified to produce highly active enzyme conjugates of HRP (Sigma, St. Louis, MO or Scripps Laboratories, La Jolla, CA), with lower degrees of conjugation (1–3 mol cytokinin/mol enzyme). Cytokinin was used in the range of 10 to 50 μmol for conjugation of 5 mg HRP. The reaction was conducted in 0.1M NaHCO$_3$, pH 9. Periodate was used in 5-fold excess. After the reaction was quenched with ethyleneglycol, NaBH$_4$ was added in 10 to 20% molar excess.

Preparation of Conjugates using 2-Morpholinoethylisocyanide and 9-(2-Carboxyethyl) Cytokinins.

Conjugation of E-9-(2-carboxyethyl)zeatin-O-β-D-glucoside to BSA was performed as follows. The 9-(2-carboxyethyl)cytokinin (55 μmol) was dissolved in 0.4 mL of dimethylformamide (DMF):DMSO (3:1), and 55 μmol of N-hydroxysuccinimide in DMF and 66 μmol of the isocyanide were added. The mixture was stirred in an amber vial at room temperature (22° C.) for 30 min. Dimethylaminopyridine (55 μmol) in DMF was then added to the mixture. The reaction mixture was next added dropwise, with stirring, to a solution of BSA in water (2 mg/mL). A control reaction was conducted similarly, but without the addition of cytokinin. The mixtures were stirred for 16 h, then dialyzed against phosphate buffered saline (PBS). The conjugates and control samples were analyzed by ultraviolet spectrometry, using $E_{268, 1\ mM}=18$ for 9-(2-carboxyethyl)zeatin-O-β-D-glucopyranoside. The degree of conjugation was estimated as 23 mol cytokinin bound per mol serum albumin.

Preparation of Polyclonal Antibodies in Mice.

Mouse antibodies were elicited in BALB/c mice by two intraperitoneal inoculations at 3-week intervals with the bovine serum albumin conjugate of E-9-(2-carboxyethyl)zeatin-O-β-D-glucopyranoside emulsified in complete Freund's adjuvant. The dosage was 50–80 μg of conjugate in 0.1–0.2 mL. The mice were bled 1 week after the second injection, and sera were obtained, and tested for antibody.

Antisera were tested by titration on wells of a polyvinylchloride assay plate which had been coated with BSA conjugate used for immunization. Diluent was BSA-PBS-"Tween". All animals responded to the incoulations by production of antibodies which bound to this solid phase. For example, antiserum from mouse #471 had half-maximal binding to the solid phase at a dilution of 1:2000, with significant binding at the highest dilution tested (1:12,500).

Table 1 illustrates the results of inhibition ELISA for the mouse polyclonal antibodies. The results show that the polyclonal antibody has binds to zeatin-O-β-D-glucopyranoside, having a carboxyethyl group substituted at the 9-position. The antibodies do not bind to zeatin lacking the glucosylated isoprenoid side chain.

TABLE 1

| Hapten | Antibody Bound (%) |
| --- | --- |
| None | 100 |
| Zeatin | 99 ± 3 |
| Carboxyethylzeatin-O-β-D-glucopyranoside | 76 ± 1 |

Preparation of monoclonal antibodies.

An antibody-producing mouse was inoculated intravenously with 80 μg of cytokinin conjugate in PBS 4 days prior to the cell fusion. Equal numbers of immune spleen cells and myeloma cells (P3-X63-Ag8.653; J. S. Kearney et al., *Journal of Immunology* 123: 1548-1550 (1979) were fused by treatment with 50% poly(ethyleneglycol) 1500, and plated at a density of $1.5 \times 10^6$ cell/mL in 96-well tissue cultures plates containing 0.2 mL/well.

Antibody-producing cultures were detected by solid-phase enzyme immunoassay 3 weeks after fusion. These cultures were expanded, and then closed by limiting dilution. Antibodies are denoted by their culture of origin (e.g., 240 for the products of cloned cell line 240). Monoclonal antibodies were characterized with regard to isotype and light-chain composition using β-galactoside conjugates of specific antibodies (Southern Biotechnology, Birmingham, AL), using myeloma proteins (Litton Bionetics, Kensington, MD) as standards.

Immunoassays.

Antibodies were screened and further analyzed by solid-phase enzyme immunoassays as follows. Polyvinylchloride assay plates (Costar, Cambridge, MA), were coated with appropriate serum albumin conjugate (made with the O-glucoside derivative or the oxidized zeatin riboside, 10 μg/mL in PBS, 50 μL/well) for 4 h at room temperature or overnight at 4°. Plates were then washed with PBS containing 0.05% "Tween"-20 (PBS-Tween). Remaining sites were blocked by incubation for 1 h with 100 μL/well of 1% BSA in PBS-"Tween" solution (BSA-PBS-"Tween"). Plates were then rewashed and stored for up to 3 weeks at 4° in PBS containing sodium azide.

Direct binding (titration) and inhibition assays were performed with antibodies dissolved in BSA-PBS-"Tween", a diluent selected to minimize nonspecific interactions with the solid phase, and to suppress binding to the solid phase by antibodies specific for serum albumin.

Inhibition assay format was used to assess antibody specificity. Antibody at an appropriate dilution determined by titration to give between 50 and 100% of maximal binding was mixed with hapten solution and preincubated for 1 h at room temperature prior to application to the coated wells. In both formats, samples (50 μL/well) were generally applied to plates in triplicate and were incubated 1 h, with shaking. Plates were emptied, washed, rinsed with distilled water, and drained. HRP-labeled rabbit anti-mouse IgG (Zymed Laboratories, South San Francisco, CA) was added at an appropriate dilution (50 μL/well) and incubated for 1 h with shaking. The plates were then washed as before, and bound HRP detected by addition of 50 μL/well of substrate (1 mM ABTS and 6.7 mM $H_2O_2$ in 60 mM sodium citrate buffer, pH 4.2). The absorbance was determined at 415 nm with a microplate reader (Model 308, Bio-Tek, Winooski, VT), generally after 15 min. In some cases, reactions were terminated by addition of 50 μL/well of 10% sodium dodecylsulfate.

Figure 4:
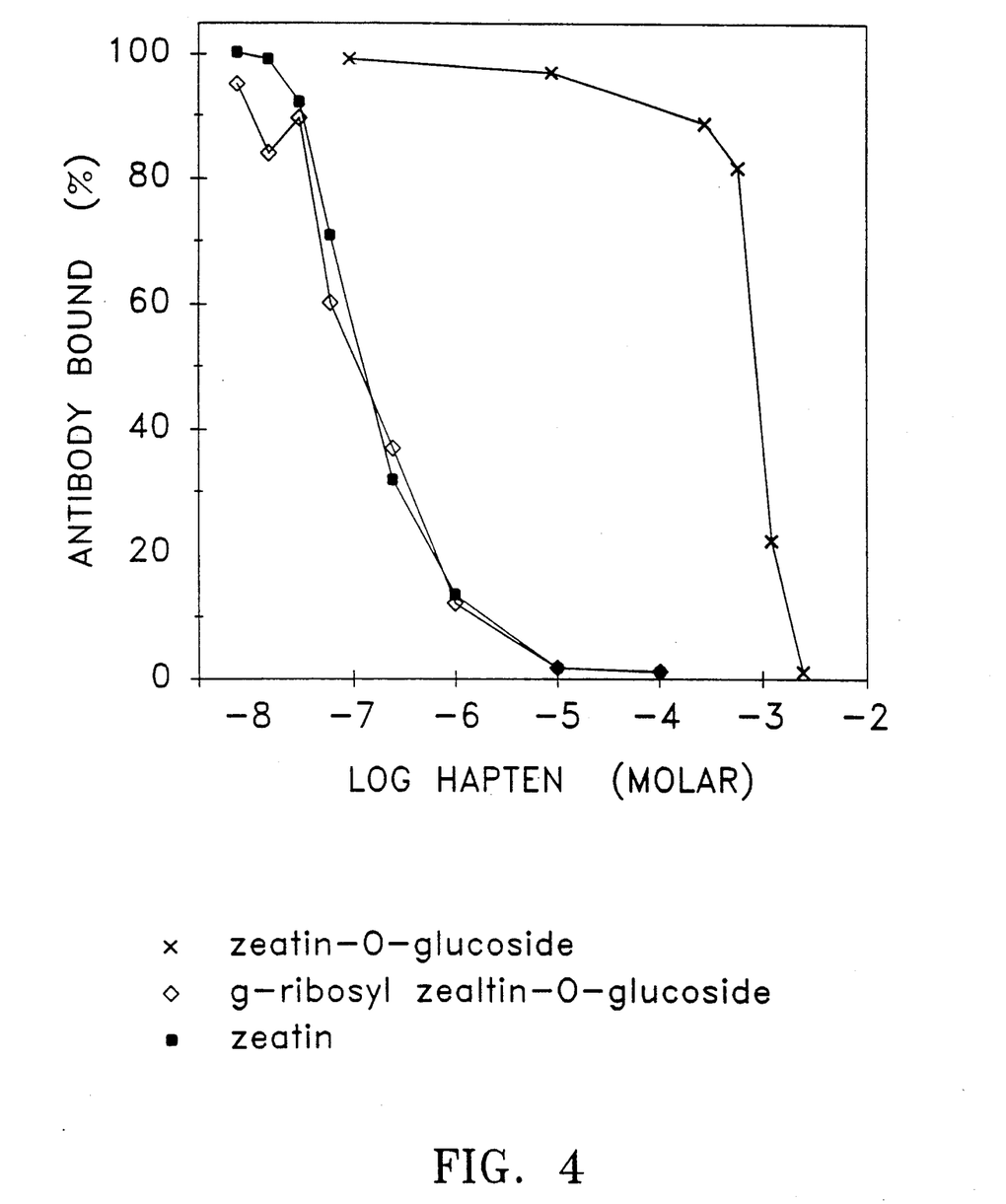
FIG. 4 shows analysis of antibody ATCC HB 9658 specificity by inhibition ELISA.

FIG. 4 shows the analysis of monoclonal antibody ATCC HB 9658 by inhibition ELISA. The figure shows that the antibody binds to zeatin-O-β-D-glucopyranoside, and is indifferent to further substitution at the 9-position (for example, a ribosyl group). The antibody does not bind significantly to zeatin lacking the O-β-D-glucopyranoside moiety (binding reduced at least 10,000-fold). This antibody was determined to be IgG1 isotype, with a kappa light chain.

Table 2 summarizes the data obtained by inhibition ELISA which demonstrates the specificity of antibody ATCC HB 9658.

TABLE 2

| Compound | $I_{50}$ (M) | Relative $I_{50}{}^a$ |
| --- | --- | --- |
| E-Zeatin-O-β-D-glucopyranoside | $8.7 \times 10^{-8}$ | 1 |
| E-Zeatin | $>1 \times 10^{-4}$ | >1100 |
| PBG | $1.2 \times 10^{-6}$ | 14 |
| O-β-D-Glucopyranosyl-E-zeatin-9-riboside | $3.0 \times 10^{-7}$ | 3.4 |
| E-Zeatin-9-β-D-glucopyranoside | $>1 \times 10^{-4}$ | >1100 |
| Isopentenyladenine | $>1 \times 10^{-3}$ | >11000 |
| Dihydrozeatin | $>1 \times 10^{-3}$ | >11000 |

$^a I_{50}$ relative to E-zeatin-O-β-D-glucopyranoside

EXAMPLE 3

This example illustrates determination of E-zeatin-O-β-D-glucopyranoside by ELISA using HRP conjugated to 9-(2-carboxyethyl)zeatin-O-β-D-glucopyranoside and monoclonal antibody ATCC HB 9658.

The HRP conjugate was prepared similarly to the BSA conjugate described above (Example 2). It had an apparent composition of 21 mol of glucoside per mol HRP. It was stored at 4°, and was stable for at least 1 year.

Competition ELISA using cytokinin conjugates of HRP was performed using polystyrene assay plates coated with mouse monoclonal antibodies specific for cytokinins. Generally, plates were first coated with 100 μL/well of 5 μg/mL rabbit anti-mouse IgG (Zymed Laboratories) and blocked with 200 μL/well of BSA-PBS-Tween, as described above. Immediately before use, assay plates were coated with 1 μg/mL of monoclonal IgG in BSA-PBS-Tween. Samples were mixed with an appropriate concentration of cytokinin-HRP conjugate and applied to assay wells in replicate (100 μL/well). After 1 h, wells were drained, washed, and rinsed. Bound conjugate was detected with ABTS substrate solution and quantified by determining absorbance at 415 nm.

Calculations were performed as follows. Assay data was fit to a logistic model. Asymptotic values were determined by inspection of the assay curves, and other coefficients were determined by linear regression. Apparent binding affinity was estimated by determining the concentration of cytokinin which resulted in 50% inhibition ($I_{50}$) of binding in either inhibition or competition ELISA formats. Relative affinities are expressed using E-zeatin riboside or E-zeatin-O-β-D-glucopyranoside as standards.

Figure 5:
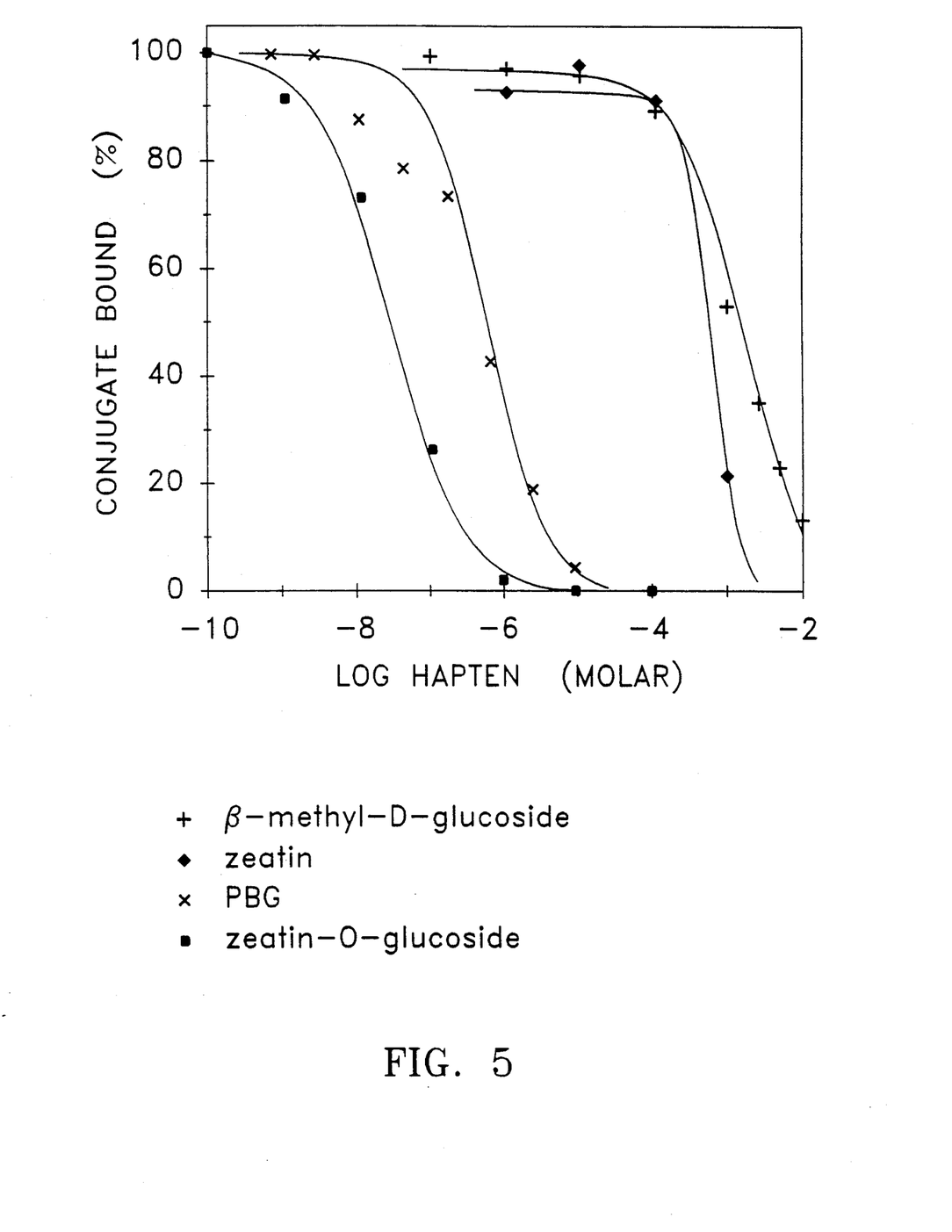
FIG. 5 shows competition ELISA using antibody ATCC HB 9658 with with E-zeatin-O-$\beta$-D-glucopyranoside, E-zeatin, E-2-methyl-4-phthalimidobut-2-enyl-$\beta$-D-glucopyranoside, and $\beta$-methyl-D-glucopyranoside as analytes.

FIG. 5 illustrates standard curves for E-zeatin, its O-β-D-glucopyranoside, E-2-methyl-4-phthalimidobut-2-enyl-β-D-glucopyranoside (PBG, the glucosylated isoprenoid side chain), and β-methyl-D-glucopyranoside in the competitive ELISA with monoclonal antibody ATCC HB 9658. It is shows that the antibody recognizes three features of the O-glucoside: the purine nucleus, the isoprenoid side chain, and the O-glucoside moiety. Absence of any one of these significantly reduces binding. Table 3 provides a tabulation of the relative binding of antibody ATCC HB 9658 to various cytokinins and PBG.

TABLE 3

| Compound | $I_{50}$ (M) | Relative $I_{50}$[a] |
|---|---|---|
| E-Zeatin-O-β-D-glucopyranoside | $2.1 \times 10^{-8}$ | 1 |
| E-Zeatin | $>1 \times 10^{-4}$ | >4800 |
| PBG | $4.9 \times 10^{-7}$ | 23 |
| O-β-D-Glucopyranosyl-E-zeatin-9-riboside | $3.5 \times 10^{-8}$ | 1.7 |
| E-Zeatin-9-β-D-glucopyranoside | $>1 \times 10^{-3}$ | >48000 |
| Isopentenyladenine | $>1 \times 10^{-4}$ | >4800 |
| Dihydrozeatin | $>1 \times 10^{-4}$ | >4800 |
| β-Methylglucoside | $>1 \times 10^{-3}$ | >48000 |

[a]$I_{50}$ relative to E-zeatin-O-β-D-glucopyranoside

FIG. 6 illustrates the competitive ELISA with monoclonal antibody from ATCC HB 9658, when the labeled zeatin and labeled E-zeatin-O-β-D-glucopyranoside are combined. The two assays can be performed simultaneously on the same sample because of the high specificity of the antibodies (crossreactivities of less than 0.1%). The samples and standard, after mixing with the labeled ligands, are incubated simultaneously on two solid phases. The first is coated with zeatin-specific antibody 94 for determination of zeatin. The second is coated with monoclonal antibody from ATCC HB 9658 for determination of zeatin-O-glucoside.

EXAMPLE 4

This example illustrates the analysis of plant extracts using the antibody ATCC HB 9658.

Preparation of Corn Root Tip Extracts.

Seeds of Zea mays were surface sterilized by brief treatment with sodium hypochlorite, then sprouted under aseptic conditions for 4–5 days at approximately 25° C. in the dark. Roots were decapped and the terminal 2 mm section excised and frozen until extracted. Samples of approximately 100 mg were homogenized in 1 mL of ice-cold extraction medium (80% methanol, 20% water, containing 1 mg/L butylated hydroxytoluene as anti-oxidant) with a Tissumizer (Tekmar, Cincinnati, OH). Extraction slurries were then spiked with [$^3$H]-dihydrozeatin (Amersham Corp., Arlington Heights, IL), about $5 \times 10^5$ cpm per g. Samples were stirred overnight in the dark at 4°. Residue was removed by centrifugation and the extract was dried in a centrifugal evaporator (Savant Instruments, Hicksville, NY).

Fractionation of Extracts.

Dried extracts were resuspended in about 0.2 mL of 40 mM ammonium acetate, pH 6.5, treated with alkaline phosphatese (0.03 units/mL for 30 min), and applied to columns (approx. $1 \times 3$ cm) of DEAE-cellulose (Whatman, Maidstone, UK). The columns were eluted with ammonium acetate buffer, and the fractions containing tritium were dried in a centrifugal evaporator and redissolved in PBS for assay. Aliquots were assayed for tritium, to determine recovery of [$^3$H]-dihydrozeatin.

Analysis of Cytokinins of Corn Root Tips.

Figure 7A:
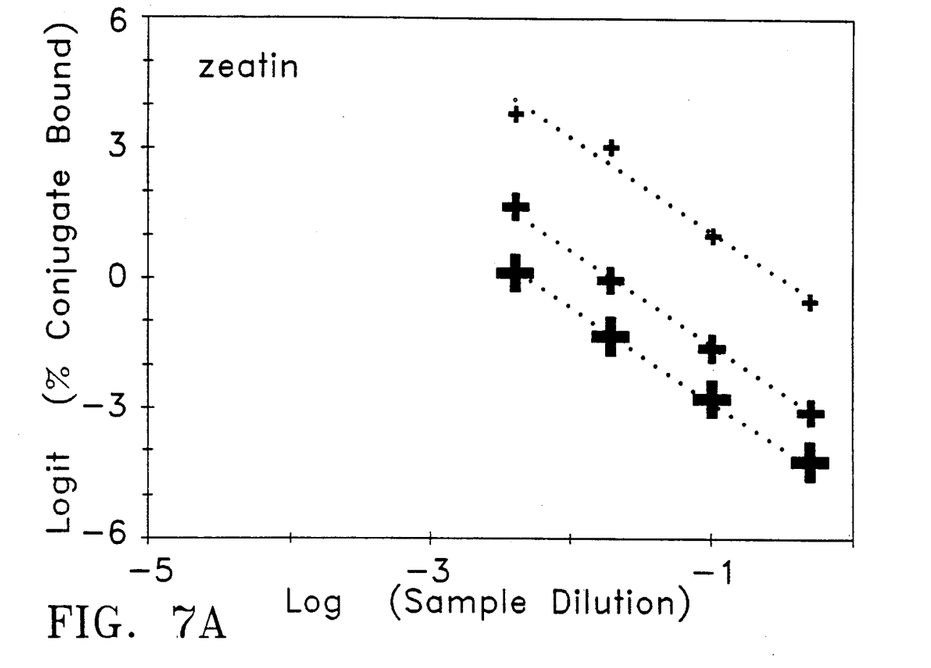
Figure 7B:
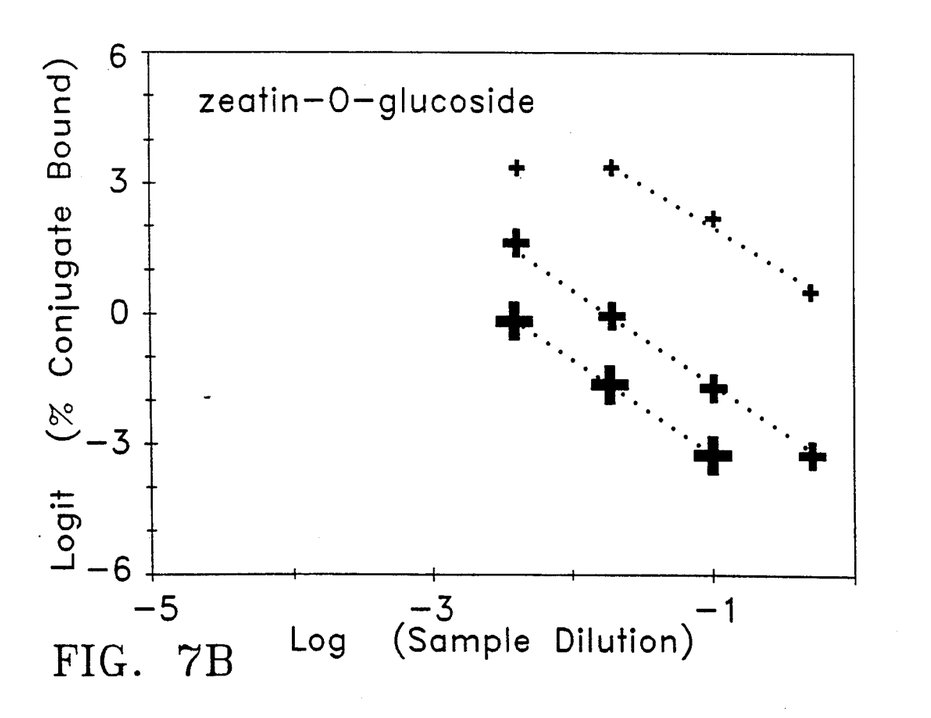

FIG. 7 illustrates representative logit-transformed data for unspiked and spiked samples. The nearly parallel lines suggest that the same antigenic substance is reacting in each assay. That is, endogenous analyte reacts with the antibodies in the same way as authentic cytokinins.

The zeatin and zeatin-O-glucoside concentrations were estimated from the fitted assay curves. The results are summarized in Table 4.

TABLE 4

| cytokinin | content (nmol/g) |
|---|---|
| zeatin | $5.5 \pm 1.5$ |
| zeatin-O-glucoside | $263 \pm 191$ |

The data are means and standard deviations from three independent samples of corn root tips. The data are expressed in terms of the non-9-substituted cytokinins. However, the assay does not distinguish among cytokinins derivatized at the 9-position (e.g., ribosides). The ratio of zeatin-O-glucoside to zeatin in these samples was $45 \pm 27$. The variation reflects differences in the samples, rather than within-assay variation. Subsequent studies have indicated that the O-glucoside concentration is dependent on the temperature during root development.

Soybean plants.

The relevant genetic composition of the six isolines derived from the Clark-L1subline are summarized in Table 5. Seeds were obtained from the USDA Soybean Germplasm Collection (Urbana, IL).

Plants grown to maturity were grown in Sunshine Mix (Fison's Western Corp., Vancouver, BC, Canada) in a greenhouse under natural lighting conditions, and were fertilized regularly with Plantex 20-20-20 (Plantco, Inc., Bramalea, Ont., CA). Leaves were sampled at various times and were cut, frozen on dry ice, and maintained at $-80°$ C. until extracted. Extraction was performed as described above for corn roots, but using 2.5 mL of extraction medium per gram fresh weight.

Fractionation of extracts. Dried extracts were fractionated as described above, with the addition of a second column fractionation (A. E. Stafford et al., Journal of Chromatography 294:485–488 (1984)) on crosslinked vinylbenzene (XAD-2, Mallinckrodt, Inc., Paris KY). The columns were eluted with ammonium acetate buffer, and the bound material was eluted with methanol. The methanol eluates were dried and redissolved in PBS for assay. Aliquots were assayed for tritium, to determine recovery of [$^3$H]-dihydrozeatin.

TABLE 5

| Strain | Genotype | Phenotype |
|---|---|---|
| CL1 | $Dt_1dt_2e_1E_2E_3Y_3$ | Normal |
| L67-1474 | $Dt_1dt_2E_1E_2E_3Y_3$ | Late maturity |
| L63-2346 | $Dt_1dt_2e_1E_2E_3Y_3$ | Yellow-green |
| L65-778 | $dt_1dt_2e_1e_2E_3Y_3$ | Delayed leaf senescence |
| L63-3016 | $dt_1dt_2e_1E_2E_3Y_3$ | Intermediate senescence |
| L66-531 | $dt_1dt_2E_1e_2E_3Y_3$ | Intermediate senescence |

Immunoassays were performed as described above in Example 3. Three of the Clark isolines, representing differing foliar senescence patterns, were examined in most detail (Table 6). The three isolines had similar zeatin:zeatin-O-glucoside ratios. Table 7 shows results obtained for the yellow-green variant (L63-2346). There was a progressive increase in the zeatin:zeatin-O-glucoside ratio as the plants senesced.

TABLE 6

| Isoline | Zeatin pmol/g | Zeatin-O-glucoside pmol/g | Ratio |
|---|---|---|---|
| C-L1 | 431 | 687 | .627 |
| L63-2346 | 291 | 538 | .540 |
| L67-1474 | 342 | 520 | .658 |

TABLE 7

| Age (weeks) | Ratio |
| --- | --- |
| 16 | .370 |
| 17 | .463 |
| 19 | .810 |
| 21 | 1.16 |

It is understood that the foregoing detailed description is given merely by way of illustration and that modification and variations may be made therein without departing from the spirit and scope of the invention.

Having thus described our invention, we claim:

1. Antibody which is specific for a cytokinin, said cytokinin possessing a glycosylated isoprenoid side chain, that is, it is able to simultaneously recognize a purine ring, an isoprenoid side chain, and a 4'-O-glycoside.

2. The antibody described in claim 1 wherein said 4'-O-glycoside of said cytokinin is 4'-O-glucoside.

3. The antibody described in claim 1 wherein said cytokinin is zeatin-O-glucoside.

4. The antibody described in claim 1 wherein said cytokinin has substitution on said purine ring.

5. The antibody described in claim 1 wherein said antibody is polyclonal.

6. The antibody described in claim 1 wherein said antibody is monoclonal.

7. A compound, 9-(2-carboxyethyl) cytokinin-O-glycoside, having the formula selected from or wherein R is glucoside, riboside, or substituted glucoside or riboside.

8. The compound of claim 7 wherein said compound is 9-(2-carboxyethyl)zeatin-O-glucoside.

9. A composition capable of raising an immunological response in an immunologically competent animal comprising a cytokinin having a purine ring, an isoprenoid side chain, and a 4'-O-glycoside coupled to an immunogenic carrier.

* * * * *

UNITED STATES PATENT AND TRADEMARK OFFICE
CERTIFICATE OF CORRECTION

PATENT NO. : 5,210,077

DATED : May 11, 1993

INVENTOR(S) : David L. Brandon and Joseph W. Corse

It is certified that error appears in the above-indentified patent and that said Letters Patent is hereby corrected as shown below:

FIG. 4, in the legend, line 2; change "g" to -- 9 --; "zealtin" to -- zeatin --.

Figure 6A:
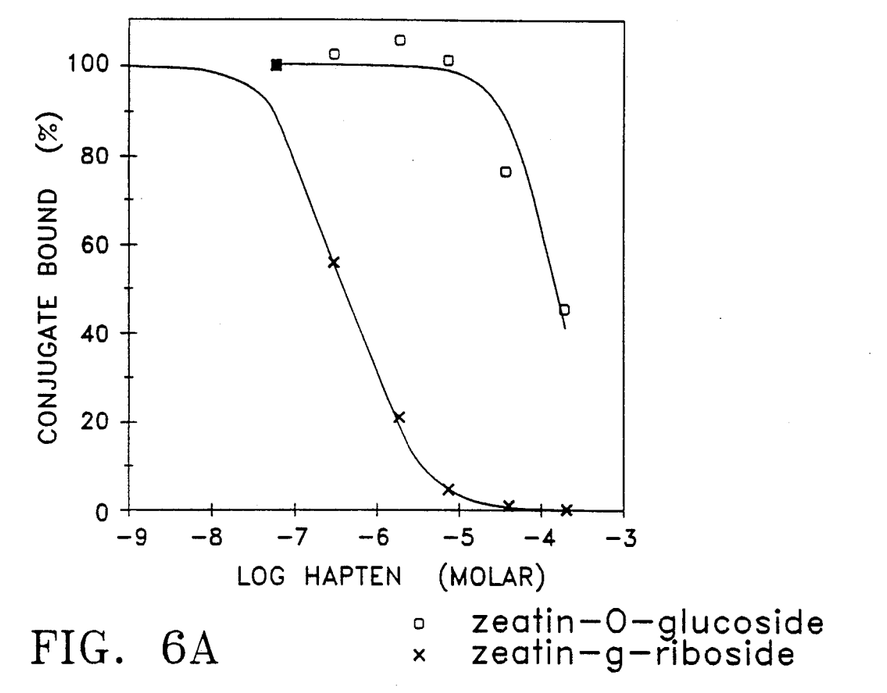

FIG. 6A, in the legend, line 2; change "g" to -- 9 --.

Figure 6B:
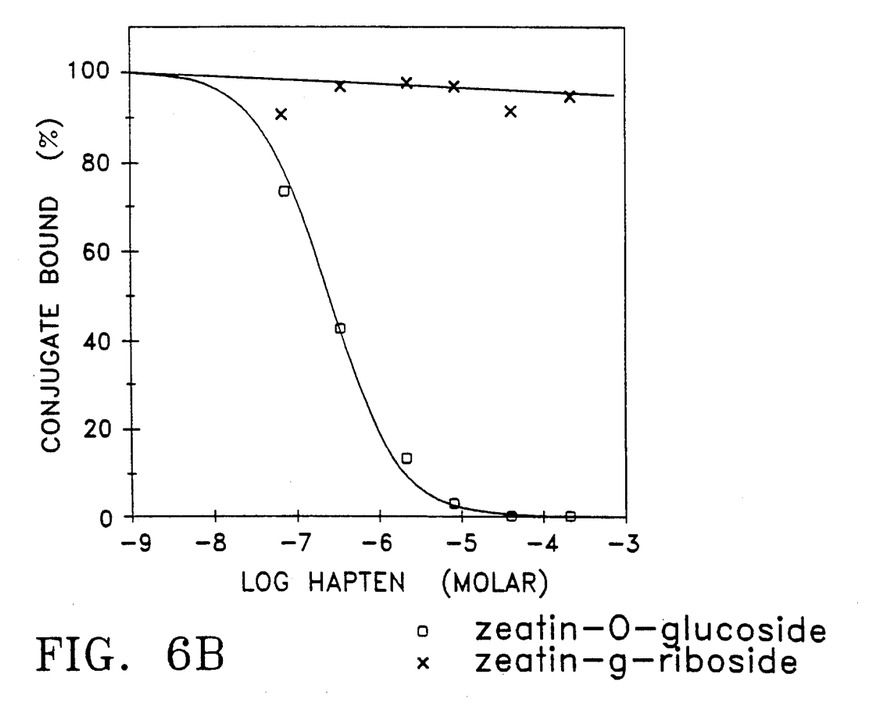

FIG. 6B, in the legend, line 2; change "g" to -- 9 --.

Column 5: line 40, change "9658" to -- 9656 --;
line 43, change "9658" to -- 9656 --;
line 50, change "9658" to -- 9656 --.

Column 12: line 25, change "9658" to -- 9656 --;

Column 17: line 63, change "9658" to -- 9656 --.

Column 18: line 5, change "9658" to -- 9656 --;
line 24, change "9658" to -- 9656 --;
line 61, change "9658" to -- 9656 --;
line 67, change "9658" to -- 9656 --.

UNITED STATES PATENT AND TRADEMARK OFFICE
CERTIFICATE OF CORRECTION

PATENT NO. : 5,210,077
DATED : May 11, 1993
INVENTOR(S) : David L. Brandon and Joseph W. Corse

It is certified that error appears in the above-indentified patent and that said Letters Patent is hereby corrected as shown below:

Column 19:  line 15, change "9658" to -- 9656 --;
            line 24, change "9658" to -- 9656 --;
            line 29, change "9658" to -- 9656 --.

Signed and Sealed this

Eighteenth Day of October, 1994

Attest:

BRUCE LEHMAN

Attesting Officer      Commissioner of Patents and Trademarks